US008702838B2

(12) United States Patent
Shimomura et al.

(10) Patent No.: US 8,702,838 B2
(45) Date of Patent: Apr. 22, 2014

(54) METHOD FOR RECOVERING METAL, AND REAGENT AND KIT FOR RECOVERY OF METAL FOR USE IN THE SAME

(75) Inventors: Yuka Shimomura, Kyoto (JP); Mayumi Yamada, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 0 days.

(21) Appl. No.: 13/437,307

(22) Filed: Apr. 2, 2012

(65) Prior Publication Data

US 2012/0251417 A1    Oct. 4, 2012

Related U.S. Application Data

(60) Provisional application No. 61/533,072, filed on Sep. 9, 2011, provisional application No. 61/538,762, filed on Sep. 23, 2011.

(30) Foreign Application Priority Data

Apr. 4, 2011  (JP) ................................ 2011-083023
Sep. 22, 2011 (JP) ................................ 2011-207906
Mar. 16, 2012 (JP) ................................ 2012-060101

(51) Int. Cl.
*C22B 3/00*   (2006.01)

(52) U.S. Cl.
USPC ................... 75/710; 75/711; 75/722; 75/743; 75/744; 423/22; 423/27; 423/87; 423/98; 423/109; 423/131

(58) Field of Classification Search
USPC ............... 423/1, 22, 27–41, 87, 98, 109, 131, 423/132; 436/73–84; 534/652; 564/19; 422/68.1; 252/182.12, 184; 75/710–745
See application file for complete search history.

(56) References Cited

U.S. PATENT DOCUMENTS

| 2,441,396 A * | 5/1948 | Corwin et al. ................ 534/586 |
| 4,087,359 A * | 5/1978 | Patron et al. .................. 210/719 |
| 4,732,887 A | 3/1988 | Obanawa et al. |
| 4,876,068 A | 10/1989 | Castaneda |
| 4,920,057 A | 4/1990 | Castaneda |
| 4,950,408 A * | 8/1990 | Duisters et al. ............... 210/660 |
| 6,896,808 B1 * | 5/2005 | Jay .................................. 210/638 |
| 2011/0020943 A1 | 1/2011 | Okamoto et al. |

FOREIGN PATENT DOCUMENTS

| CN | 85 1 08961 A | | 6/1986 |
| DE | 19510229 | * | 9/1996 |
| EP | 0319615 A1 | | 6/1989 |
| EP | 0536059 A2 | | 4/1993 |
| JP | 58-049490 A | | 3/1983 |
| JP | 63-067529 B | | 12/1988 |
| JP | 2-034655 B | | 8/1990 |
| JP | 5-232028 A | | 9/1993 |
| JP | 2569157 B2 | | 1/1997 |
| JP | 9-047768 A | | 2/1997 |
| JP | 10-113677 A | | 5/1998 |
| JP | 11-042469 A | | 2/1999 |
| JP | 2969226 B2 | | 8/1999 |
| JP | 2969226 A | | 11/1999 |
| JP | 2000-136371 A | | 5/2000 |
| JP | 2003-194798 A | | 7/2003 |
| JP | 2003-322596 A | | 11/2003 |
| JP | 2006-253420 A | | 9/2006 |
| JP | 2009-294024 A | | 12/2009 |
| JP | 2009-294060 A | | 12/2009 |
| JP | 2010-156619 A | | 7/2010 |
| WO | 2009/116669 A1 | | 9/2009 |

OTHER PUBLICATIONS

Ministry of the Environment, Japan, "Mercury Analysis Manual," Mar. 2004.
Andoh et al., "Solid Phase Extraction of Ni and Cd by Chelating Cellulose Functionalized with Thiolactic Acid," Bunseki Kagaku, 57: 1027-1032 (2008).
Hayashi et al., "Study on Quantitative Analysis of Heavy Metals in Waste Water by Chelating resin disk preconcentration/ICP-AES," Annual Report of the Kawasaki Municipal Research Institute for Environmental Protection 45-50 (2003).
Itoh et al., "Determination of Trace Metals in Coastal Seawater around Okinawa and Its Multielement Profiling Analysis," Bunseki Kagaku, 58: 257-263 (2009).
Matsunaga, "Recognition, separation and concentration of metal ions with chelating resins or chelating reagent impregnated resins (Review)," Bunseki Kagaku, 50: 89-106 (2000).
Nagai et al., "The precipitation chromatography of several metal cations with thiooxine impregnated filter paper," Bunseki Kagaku, 24: 184-187 (1975).

(Continued)

*Primary Examiner* — Steven Bos
(74) *Attorney, Agent, or Firm* — Morgan, Lewis & Bockius LLP

(57) ABSTRACT

A method for recovering a metal, capable of recovering a metal easily without requiring the use of an organic medium, is provided. A complex between a chelating agent and a metal present in a sample is formed in a mixture prepared by mixing the chelating agent and the sample under pH conditions where the chelating agent can be insoluble in an aqueous medium. Then, the complex is recovered from the mixture, and further, the metal is recovered by dissolving the recovered complex in an aqueous medium under pH conditions that are different from the pH conditions where the chelating agent can be insoluble in an aqueous medium. By this method, a metal can be recovered easily without requiring the use of the use of an organic medium.

12 Claims, No Drawings

(56) References Cited

OTHER PUBLICATIONS

Oikawa et al. "Preconcentration of Heavy Metal Ions with Thermo-Sensitive Chitosan and Atomic Absorption Spectrometric Determination of Trace Cadmium in Water," Bunseki Kagaku, 56: 721-728 (2007).

Sakamoto et al., "Pretreatment Method for Determination of Trace Elements in Seawater Using Solid Phase Extraction Column Packed with Polyamino-Polycarboxylic Acid Type Chelating Resin," Bunseki Kagaku, 55: 133-139 (2006).

Shamsipur et al., "Solid phase extraction and determination of sub-ppb levels of hazardous Hg2+ions," Journal of Hazardous Materials B117, 129-133 (2005).

Takeuchi et al., "An Accurate and Rapid Analysis for Lead in Urine Using Solid Phase Extraction Column Packed with a Functional Chelating Resin," Japanese Journal of Occupational Medicine and Traumatology, 55: 15-19 (2007).

Ueno et al., "Bismuthiol II," Handbook of Organic Analytical Reagents, CRC Press, 479-485 (1992).

Ueno et al., "Dithizone and Related Agents," Handbook of Organic Analytical Reagents, CRC Press, 431-443 (1992).

Ueno et al., "Thiothenoyltrifluoroacetone," Handbook of Organic Analytical Reagents, CRC Press, 487-492 (1992).

Ueno et al., "Thioxine," Handbook of Organic Analytical Reagents, CRC Press, 445-456 (1992).

Watanabe et al., "Spectrophotometric Determination of Small Amounts of Cadmium(II) Using Formation of Zinc(II) Complex with Anionic Porphyrin as an Indicator Reaction," Bunseki Kagaku, 59: 589-595 (2010).

Yamada et al., "Simultaneous determinations of Cu, Cd and Pb in river-water samples by multielement isotope dilution/ICP-MS with the aid of chelating resin preconcentration," Bunseki Kagaku, 50: 433-439 (2001).

Yamamoto et al., "Highly Efficient and Automatic Collection/Concentration with Chelating Resin for Inductively Coupled Plasma Atomic Emission Spectroscopy," Bunseki Kagaku, 55: 715-720 (2006).

Yokoyama et al., "Determination of Aluminum in Water Samples by Flame AAS after Extraction of 8-quinolinol Complex with Nitrobenzene," Bunseki Kagaku, 55: 757-763 (2006).

Zhu, "Development of Chelating Resin-Packed Minicolumn for Multielement Preconcentration and Determination of Trace Metals in Natural Water," Bunseki Kagaku, 56: 895-896 (2007).

Nezhadali et al., "Graphite Furnace Atomic Absorption Spectrometric Determination of Cadmium after Solid-Liquid Extraction with Dithizone", Bull, Chem. Soc. Ethiop., 23(2):257-261 (2009).

\* cited by examiner

METHOD FOR RECOVERING METAL, AND REAGENT AND KIT FOR RECOVERY OF METAL FOR USE IN THE SAME

CROSS-REFERENCE TO RELATED APPLICATION

This application claims priority from Japanese Patent Application Nos. 2011-083023, 2011-207906, and 2012-060101, filed on Apr. 4, 2011, Sep. 22, 2011, and Mar. 16, 2012, respectively and U.S. Provisional Application Ser. Nos. 61/533,072 and 61/538,762, filed on Sep. 9, 2011 and Sep. 23, 2011, respectively, the entire subject matters of which are incorporated herein by reference.

BACKGROUND OF THE INVENTION

The present invention relates to a method for recovering a metal and a reagent and kit for recovery of a metal for use in the same. The present invention also relates to a method for analyzing a metal and an analysis apparatus for use in the same.

It is known that metals such as mercury, cadmium, lead, and arsenic accumulate in human bodies, which results in adverse effects on health. Therefore, it is important to analyze metals in biological samples such as urine and the like and samples of food and beverage such as water and the like.

In analyzing a metal, generally, as a pretreatment, foreign substances are removed from a sample, a metal is separated from the resulting sample, and the separated metal is analyzed. In the pretreatment, a solvent extraction is widely used. The solvent extraction is a method in which a metal in a sample is extracted into an organic medium by utilizing the polarity of a chelating agent to be bound to the metal according to the difference in distribution coefficient of the metal to an aqueous medium and the organic medium. The metal can be further concentrated by evaporating the organic medium after the extraction. As a specific example of the solvent extraction, a dithizone method using, as the chelating agent, 1,5-diphenyl-3-thiocarbazone (hereinafter, also referred to as "dithizone") that is insoluble in an aqueous medium under acidic conditions is defined in JIS, for example (see, Mercury Analysis Manual, Ministry of the Environment, March 2004, Japanese Patent No. 2969226). In the dithizone method, first, dithizone and a liquid sample such as urine are mixed under acidic conditions, and a complex between the dithizone and a metal present in the liquid sample is formed in the mixture. Subsequently, an organic medium such as carbon tetrachloride or chloroform is added to the mixture. Then, the complex is extracted into the organic medium because the distribution coefficient of the complex to the aqueous medium is different from that of the complex to the organic medium. Thereafter, this organic medium is recovered. Thus, the metal is recovered as the complex from the liquid sample. When the organic medium is evaporated, the metal can be further concentrated.

However, it is essential to use an organic medium in the conventional solvent extraction method as mentioned above. In the case of using an organic medium, handling thereof is complicated, and there is a risk that a waste liquid thereof affects the environment. Moreover, in order to concentrate the metal extracted using the organic medium, a decompressor for evaporating the organic medium is required, for example.

BRIEF SUMMARY OF THE INVENTION

The present invention is intended to provide a method for recovering a metal without requiring the use of an organic medium.

In order to achieve the aforementioned object, the present invention provides a method for recovering a metal, the method including the steps of: forming a complex between a chelating agent and a metal present in a sample in a mixture prepared by mixing the chelating agent and the sample under pH conditions where the chelating agent can be insoluble in an aqueous medium; recovering the complex from the mixture; and recovering the metal by dissolving the recovered complex in an aqueous medium under pH conditions that are different from the pH conditions where the chelating agent can be insoluble in an aqueous medium.

The present invention also provides a reagent for recovery of a metal, for use in a method for recovering a metal of the present invention, the reagent containing: a chelating agent.

The present invention also provides a kit for recovery of a metal, for use in the method for recovering a metal of the present invention, the kit including: a chelating agent; and a pH adjusting reagent.

The present invention also provides an analysis apparatus including: a pH adjusting unit for adjusting a pH; a mixing unit for mixing a chelating agent and a sample; a complex recovering unit for recovering a complex between the chelating agent and a metal present in the sample from a mixture containing the chelating agent and the sample; an adding unit for adding an aqueous medium to the recovered complex; a metal recovering unit for recovering the metal present in the complex; and an analyzing unit for analyzing the recovered metal, wherein the analysis apparatus is for use in a method for analyzing a metal.

According to the present invention, a metal can be recovered easily by utilizing the difference in solubility of the chelating agent in an aqueous medium according to the difference in pH conditions without substantially using an organic medium. Therefore, the present invention is useful in clinical examinations of samples derived from biological bodies and environmental testing, for example.

DETAILED DESCRIPTION OF THE INVENTION

Method for Recovering Metal

The method for recovering a metal (hereinafter referred to as the "metal recovering method") of the present invention is, as mentioned above, a method for recovering a metal, the method including the steps of: forming a complex between a chelating agent and a metal present in a sample in a mixture prepared by mixing the chelating agent and the sample under pH conditions where the chelating agent can be insoluble in an aqueous medium; recovering the complex from the mixture; and recovering the metal by dissolving the recovered complex in an aqueous medium under pH conditions that are different from the pH conditions where the chelating agent can be insoluble in an aqueous medium.

In the metal recovering method of the present invention, the chelating agent preferably is a chelating agent comprising a sulfur-containing group. The sulfur-containing group is a functional group having a sulfur atom. The sulfur-containing group may be a thioketone group or comprises a thioketone group, for example. The thioketone group is not particularly limited and examples thereof include a thiocarbazone group, a thiosemicarbazone group, a thiocarbadiazone group, a thiourea group, a thiosemicarbazide group, and a rubeamate group.

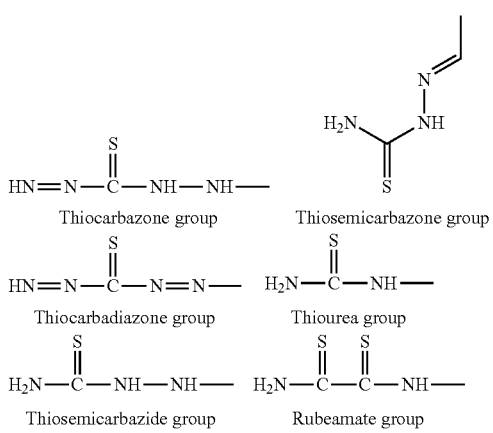

The chelating agent preferably is represented by the following structural formula (1) or (2), for example.

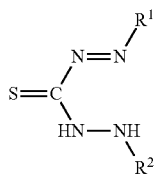

In the structural formula (1), $R^1$ and $R^2$ each represents a phenyl group. That is, the chelating agent represented by the structural formula (1) is a chelating agent comprising a thiocarbazone group and can be 1,5-diphenyl-3-thiocarbazone (dithizone). The chelating agent represented by the structural formula (1) may be, for example, a salt.

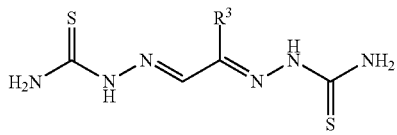

In the structural formula (2), $R^3$ represents hydrogen, an alkyl group, or a phenyl group. The chelating agent represented by the structural formula (2) may be, for example, a salt.

The alkyl group is not particularly limited, and examples thereof include straight-chain or branched alkyl groups. The carbon number of the alkyl group is, for example, from 1 to 6. Examples of the straight-chain or branched alkyl groups include a methyl group, an ethyl group, a n-propyl group, an isopropyl group, a n-butyl group, an isobutyl group, a sec-butyl group, a tert-butyl group, a n-pentyl group, an isopentyl group, a neopentyl group, a n-hexyl group, an isohexyl group, a n-heptyl group, a n-octyl group, a n-nonyl group, and a n-decyl group. Any hydrogen in the alkyl group may be substituted, for example.

Any hydrogen in the phenyl group may be substituted, for example. For example, the hydrogen in the phenyl group may be substituted by halogen or an alkali metal such as sodium or potassium when substituted.

The chelating agent represented by the structural formula (2) is, for example, a chelating agent comprising a thiosemicarbazone group, and examples thereof include glyoxaldithiosemicarbazone and (1E,2E)-aminocarbothioyl hydrazono phenylethanal thiosemicarbazone.

In the metal recovering method of the present invention, the chelating agent preferably is a chelating agent comprising a sulfur-containing group as mentioned above. The sulfur-containing group can be, for example, a thioketone group. The chelating agent comprising a thioketone group can be, for example, a chelating agent comprising at least one selected from the group consisting of a thiocarbazone group, a thiosemicarbazone group, a thiocarbadiazone group, a thiourea group, a thiosemicarbazide group, and a rubeamate group. As specific examples of the chelating agent, the following chelating agents are illustrated. In the present invention, the following chelating agents are mere examples, and the present invention is not limited thereby.

(a1) Chelating agent comprising a thiocarbazone group, e.g., 1,5-di(2-naphtyl)thiocarbazone;

(a2) Chelating agent comprising a thiosemicarbazone group, e.g., acetone thiosemicarbazone, acetophenone thiosemicarbazone;

(a3) Chelating agent comprising a thiocarbadiazone group, e.g., diphenylthiocarbadiazone;

(a4) Chelating agent comprising a thiourea group, e.g., 1-acetyl-2-thiourea, guanyl thiourea, 1,3-bis(dimethylaminopropyl)-2-thiourea, tetramethyl thiourea, N,N'-diethyl thiourea, N,N'-diisopropyl thiourea, N,N'-dibutyl thiourea, 1,3-bis(dimethylaminopropyl)-2-thiourea, N-allyl-N'-(2-hydroxyethyl)thiourea, N,N'-bis(2-hydroxyethyl)thiourea, diacetyl thiourea, phenyl thiourea, N,N'-diphenyl thiourea, mono-o-tolyl thiourea, N,N'-di-o-tolyl thiourea, benzoyl thiourea;

(a5) Chelating agent comprising a thiosemicarbazide group, e.g., phenylthiosemicarbazide, 4-phenylthiosemicarbazide, 4-methylthiosemicarbazide, thiosemicarbazide;

(a6) Chelating agent comprising a rubeamate group, e.g., dithiooxamide (rubeanic acid).

In the metal recovering method of the present invention, the metal to be recovered is not particularly limited. Examples thereof include Bi (bismuth), Hg (mercury), Cd (cadmium), Pd (palladium), Zn (zinc), Tl (thallium), Ag (silver), Pb (lead), and As (arsenic). The form of the metal in the sample is not particularly limited and may be, for example, a single metal, an alloy of metals, or a metal-containing compound. The metal-containing compound may be, for example, a metal-containing organic compound or a metal-containing inorganic compound. In the case where the metal is Hg, Hg may be, for example, organic mercury or inorganic mercury. In the metal recovering method of the present invention, the metal to be recovered may be, for example, one kind or two or more kinds. In the metal recovering method of the present invention, two or more kinds of metals can be recovered at the same time by a single recovering treatment, for example.

In the metal recovering method of the present invention, the sample is not particularly limited. Examples thereof include a sample derived from a biological body, a sample derived from the environment, a chemical substance, and a pharmaceutical. Examples of the chemical substance include reagents, pesticides, and cosmetics. The sample derived from a biological body is not particularly limited, and examples thereof include urine, blood, hair, and umbilical cords. Examples of the blood sample include erythrocytes, whole blood, sera, and plasma. Among them, the urine sample is preferable. The sample derived from the environment is not particularly limited, and examples thereof include an organism, food, water, the ground, and atmosphere and air.

Examples of the organism include animals such as the human and fish and shellfish and plants. Examples of the food sample include a fresh food and a processed food. Examples of the water sample include drinking water, groundwater, river water, seawater, and domestic sewage.

A fluid sample (liquid sample) is preferable as the sample because it can be handled easily, for example. An undiluted liquid or a diluted liquid obtained by suspending, dispersing, or dissolving the sample in a medium may be used as the liquid sample, for example. In the case where the sample is a solid, a diluted liquid obtained by suspending, dispersing, or dissolving the solid in a medium may be used as the liquid sample, for example. Hereinafter, the medium is referred to as a dilution medium. The dilution medium is not particularly limited, and examples thereof include water and a buffer solution. The buffer solution is not particularly limited and examples thereof include a tris buffer solution, a phosphate buffer solution, an acetate buffer solution, a borate buffer solution, a citrate buffer solution, a veronal buffer solution, and various Good buffer solutions. The concentration of the buffer solution is not particularly limited and is, for example, from about 10 to about 100 mmol/L.

According to the present invention, it is not necessary to use an organic medium as mentioned above, and the recovery rate and concentration rate of a metal can be improved compared with those obtained by the conventional method using an organic medium, for example.

(1) Step of Forming a Complex

The step of forming a complex is a step of forming a complex between a chelating agent and a metal present in a sample in a mixture prepared by mixing the chelating agent and the sample under pH conditions where the chelating agent can be insoluble in an aqueous medium. Hereinafter, the "pH conditions where the chelating agent can be insoluble in an aqueous medium" may also referred to as the "pH conditions for insolubilization".

The chelating agent can maintain the state of being undissolved in the mixture under the pH conditions for insolubilization. Therefore, when a metal is present in the sample, a complex between the chelating agent and the metal present in the sample is formed in the mixture. The chelating agent is, for example, preferably in the state of not being completely dissolved in the mixture and, however, may be in the state of being partially dissolved in the mixture. In the latter case, for example, even where the chelating agent is partially dissolved in the mixture, it is only necessary that the amount of the remaining chelating agent present in the mixture in the state of being undissolved therein is the amount capable of forming a complex with the metal.

The pH conditions for insolubilization can be set as appropriate according to the kinds of the chelating agent to be used and the metal to be recovered. In the step of forming a complex, the pH conditions for insolubilization are not particularly limited. The pH conditions for insolubilization can be, for example, acidic conditions (e.g., about pH 5 or less), neutral conditions (e.g., about pH 6 to about pH 7), and alkaline conditions (e.g., more than about pH 7 to about pH 8 or less). In an exemplary embodiment, the upper limit thereof is, for example, about pH 8, and the lower limit thereof is, for example, about pH 1. Specific examples thereof include pH 1 to 8 with all pH values in-between, such as pH 2 to 8, such as pH 1 to 2.

It is only necessary that the mixture containing the chelating agent and the sample is substantially an aqueous medium. The aqueous medium is a non-organic medium, means a so-called aqueous liquid, and can also be referred to as an aqueous solvent. "Substantially an aqueous medium" means that it may be an aqueous medium containing a trace amount of an organic medium (so-called organic solvent) as compared to the pure aqueous medium, for example.

The form of the chelating agent at the time of mixing with the sample is not particularly limited, and the chelating agent may be in a dry state (or also referred to as a solid state) or in a liquid state, for example. In the latter case, the chelating agent is preferably a chelating agent-dispersion liquid obtained by dispersing the chelating agent in a non-organic medium in which the chelating agent cannot be dissolved. Hereinafter, the non-organic medium in which the chelating agent is dispersed is referred to as a "dispersion medium". The dispersion medium is, for example, a non-organic medium (aqueous medium) under the pH conditions for insolubilization. In the case where the pH conditions for insolubilization are acidic conditions, examples of the dispersion medium include an acid, an acid aqueous solution, and a buffer solution under acidic conditions. In the case where the pH conditions for insolubilization are alkaline conditions, examples of the dispersion medium include an alkali, an alkali aqueous solution, and a buffer solution under alkaline conditions. In the case where the pH conditions for insolubilization are neutral conditions, examples of the dispersion medium include, in addition to water, a neutral aqueous solution, and a buffer solution under neutral conditions, an acid, an acid aqueous solution, a buffer solution under acidic conditions, an alkali, an alkali aqueous solution, and a buffer solution under alkaline conditions.

The acid is not particularly limited, and examples thereof include hydrochloric acid, sulfuric acid, acetic acid, boric acid, phosphoric acid, and citric acid. The acid aqueous solution can be, for example, one obtained by diluting an acid with water or a buffer solution. The buffer solution for use in the dilution of the acid is not particularly limited, and any of the above-mentioned general buffer solutions can be used. The concentration of the acid in the acid aqueous solution is not particularly limited and is, for example, more than about 0N to about 1N or less, such as from about 0.01N to about 0.1N. The buffer solution under acidic conditions is not particularly limited, and examples thereof include a citrate buffer solution, an acetate buffer solution, a phosphate buffer solution, and Good buffer solutions. The concentration of the buffer solution under acidic conditions is not particularly limited and is, for example, from about 10 to about 100 mmol/L.

The neutral aqueous solution is not particularly limited, and examples thereof include a physiological saline solution, a phosphate buffer solution, and a tris buffer solution. The buffer solution under neutral conditions is not particularly limited. The concentration of the buffer solution under neutral conditions is not particularly limited and is, for example, from about 10 to about 100 mmol/L.

The alkali is not particularly limited, and examples thereof include sodium hydroxide and potassium hydroxide. The alkali aqueous solution can be, for example, one obtained by diluting an alkali with water or a buffer solution. The buffer solution for use in the dilution of the alkali is not particularly limited, and any of the above-mentioned general buffer solutions can be used. The concentration of the alkali in the alkali aqueous solution is not particularly limited and is, for example, more than about 0N to about $7 \times 10^{-3}$N or less. The buffer solution under alkaline conditions is not particularly limited, and examples thereof include Tris-NaOH, Tris-HCl, a carbonate buffer, and Good buffer solutions. The concentration of the buffer solution under alkaline conditions is not particularly limited and is, for example, from about 10 to about 100 mmol/L.

A method for mixing the sample and the chelating agent is not particularly limited. The method may be, for example, (1a) mixing the sample where the pH conditions have been previously adjusted to the pH conditions for insolubilization and the chelating agent, (1b) mixing the chelating agent where the pH conditions have been previously adjusted to the pH conditions for insolubilization and the sample, or (1c) mixing a non-organic medium under the pH conditions for insolubilization, the chelating agent, and the sample.

In the method (1a), for example, the mixture under the pH conditions for insolubilization can be prepared by mixing the sample where the pH conditions have been adjusted to the pH conditions for insolubilization and the chelating agent, and thus the complex can be formed in the mixture. At that time, for example, the pH of the sample is adjusted so that the mixture prepared by mixing the chelating agent and the sample is under the pH conditions for insolubilization.

In the case where the pH conditions for insolubilization are acidic conditions, a method for adjusting the pH conditions of the sample to acidic conditions is not particularly limited, for example. The adjustment can be performed by adding an acidic regent to the sample, for example. Examples of the acidic reagent include an acid, an acid aqueous solution, and a buffer solution under acidic conditions. The acid is not particularly limited, and examples thereof include hydrochloric acid, sulfuric acid, citric acid, boric acid, phosphoric acid, and acetic acid. The acid aqueous solution can be, for example, one obtained by diluting an acid with water or a buffer solution. The buffer solution for use in the dilution of the acid is not particularly limited, and any of the above-mentioned general buffer solutions can be used. The concentration of the acid in the acid aqueous solution is not particularly limited and is, for example, from about 0.01N to about 5N. The buffer solution under acidic conditions is not particularly limited, and examples thereof include a citrate buffer solution, an acetate buffer solution, a phosphate buffer solution, and Good buffer solutions. The concentration of the buffer solution under acidic conditions is not particularly limited and is, for example, from about 10 to about 100 mmol/L.

In the case where the pH conditions for insolubilization are alkaline conditions, a method for adjusting the pH conditions of the sample to alkaline conditions is not particularly limited, for example. The adjustment can be performed by adding an alkaline reagent to the sample, for example. Examples of the alkaline regent include an alkali, an alkali aqueous solution, and a buffer solution under alkaline conditions such as mentioned above.

In the case where the pH conditions for insolubilization are neutral conditions, a method for adjudging the pH conditions of the sample to neutral conditions is not particularly limited, for example. The adjustment can be performed by adding the acidic reagent, the alkaline reagent, or a neutral reagent to the sample according to the original pH conditions of the sample, for example. Examples of the neutral reagent include water, a neutral aqueous solution, and a buffer solution under neutral conditions such as mentioned above.

In the method (1b), for example, the mixture under the pH conditions for insolubilization can be prepared by mixing the sample and the chelating agent where the pH conditions have been adjusted to the pH conditions for insolubilization, and thus the complex can be formed in the mixture. At that time, for example, the pH of the chelating agent is adjusted so that the mixture prepared by mixing the sample and the chelating agent is under the pH conditions for insolubilization.

A method for adjusting the pH conditions of the chelating agent to the pH conditions for insolubilization is not particularly limited. Specifically, by dispersing the chelating agent in a dry state in a non-organic medium in which the chelating agent cannot be dissolved, the chelating agent-dispersion liquid where the pH conditions have been adjusted to the pH conditions for insolubilization can be obtained. As the non-organic medium in which the chelating agent is dispersed, any of the above-mentioned dispersion media such as the acidic reagent, the alkaline regent, and the neutral reagent can be used, for example.

The chelating agent in a dry state is superior in dispersibility in a non-organic medium, for example. Therefore, a dried chelating agent obtained by freeze-drying or drying under reduced pressure is preferable. A method for producing the dried chelating agent is not particularly limited, and for example, the dried chelating agent is obtained by mixing a chelating agent into an organic medium, and thereafter freeze-drying the mixture or drying the mixture under reduced pressure. The organic medium is not particularly limited, and for example, t-butyl alcohol or 2-propanol can be used.

In the method (1c), for example, the mixture under the pH conditions for insolubilization can be prepared by mixing the non-organic medium under the pH conditions for insolubilization, the chelating agent, and the sample, and thus the complex can be formed in the mixture. At that time, for example, the pH of the non-organic medium is adjusted so that the mixture prepared by mixing the chelating agent, the sample, and the non-organic medium is under the pH conditions for insolubilization.

As the non-organic medium under the pH conditions for insolubilization, the acidic reagent, the alkaline reagent, the neutral reagent, or the like such as mentioned above can be used, for example.

A method for mixing the chelating agent and the sample is not particularly limited, and examples thereof include conventional methods such as mixing by repeatedly turning upside down, mixing by vibrating, and mixing by ultrasound.

The concentration of the chelating agent in the mixture is not particularly limited and is, for example, in the range from 0.1 to 2 mg. Specifically, the concentration of the chelating agent represented by the structural formula (1) in the mixture is, for example, in the range from 0.1 to 1.5 mg/mL, preferably from 0.1 to 0.3 mg/mL. The concentration of the chelating agent represented by the structural formula (2) in the mixture is, for example, in the range from 0.3 to 2 mg/mL, preferably from 1 to 2 mg/mL.

The concentration of the sample in the mixture is not particularly limited and is, for example, in the range from 0.1 to 100 μg/L. The concentration of an undiluted sample in the mixture is preferably in the above-described range.

The ratio between the chelating agent and the sample in the mixture is not particularly limited and is, for example, in the range from 0.1 to 2 mg of the chelating agent per 1 mL of the sample. Specifically, with respect to the chelating agent represented by the structural formula (1), the ratio is, for example, in the range from 0.1 to 1.5 mg of the chelating agent, preferably from 0.1 to 0.3 mg of the chelating agent, per 1 mL of the sample, and with respect to the chelating agent represented by the structural formula (2), the ratio is, for example, in the range from 0.3 to 2 mg of the chelating agent, preferably from 1 to 2 mg of the chelating agent, per 1 mL of the sample.

The mixture may contain other components besides the chelating agent and the sample. The other components are not particularly limited, and examples thereof include an oxidizing agent and a reducing agent. The oxidizing agent can be used for improving reactivity of a reaction for forming a complex between the chelating agent and the metal, for example. The reducing agent can be used for canceling the excess amount of the oxidizing agent when the mixture contains the excess amount of the oxidizing agent, for example.

The treatment conditions for forming the complex are not particularly limited, and the treatment temperature is, for example, room temperature, and the treatment time is, for example, from 10 seconds to 120 minutes. Specifically, the treatment time is, for example, preferably in the range from 10 seconds to 10 minutes, particularly preferably from 10 seconds to 5 minutes.

(2) Step of Recovering Complex

In the step of recovering a complex, the complex formed in the step of forming a complex is recovered from the mixture.

As mentioned above, the chelating agent can maintain the state of being undissolved in the mixture under the pH conditions for insolubilization. Therefore, the complex between the chelating agent and the metal is also present in the mixture in the state of being undissolved therein. Thus, in this step of recovering a complex, the undissolved complex being present in the mixture is recovered.

A method for recovering the complex is not particularly limited, and a conventionally known method for separating a solid from a liquid can be employed, for example. Examples of the method include a centrifugal treatment, a filtration treatment, a precipitation treatment, a membrane separation treatment, an adsorption treatment, and a freeze-drying treatment. The treatment conditions for recovering the complex are not particularly limited and can be set as appropriate according to the kind or amount of the complex, for example. In the case where the complex is recovered by the centrifugal treatment, the treatment conditions can be, for example, the centrifugal acceleration in the range from 19,600 to 29,400 m/s$^2$ (2,000 to 3,000×g), the temperature in the range from 4° C. to room temperature, and the time in the range from 1 to 10 minutes. The complex can be recovered by removing a supernatant after the centrifugation, for example. In the case where the complex is recovered by the filtration treatment, a filter to be used is not particularly limited, for example, and examples thereof include a filter paper, filter powder, and a membrane filter. After the filtration treatment, a fraction that has not passed through the filter can be recovered as the complex.

(3) Step of Recovering Metal

In the step of recovering the metal, the metal is recovered by dissolving the recovered complex in an aqueous medium under pH conditions that are different from the pH conditions where the chelating agent can be insoluble in an aqueous medium. It is only necessary that the pH conditions in the step of recovering the metal are pH conditions that are different from the pH conditions for insolubilization set in the step of forming a complex, and specifically, it is preferably the pH conditions where the chelating agent can be soluble in an aqueous medium. The pH conditions where the chelating agent can be soluble in an aqueous medium are also referred to as the pH conditions for solubilization. The pH conditions for solubilization isare for example, alkaline conditions.

The chelating agent is dissolved under the pH conditions for solubilization. Therefore, by mixing the recovered complex into an aqueous medium under the pH conditions for solubilization, the chelating agent in the state of being the complex can be dissolved in the aqueous medium. The aqueous medium in which the complex has been dissolved is also referred to as a complex aqueous solution. It is preferred that the complex is completely dissolved in the aqueous solution, for example, and however, the complex may partially remain in the state of being undissolved in the aqueous solution. It is preferred that the amount of the undissolved complex is the detection limit or less, for example.

The pH conditions for solubilization in the step of recovering the metal are not particularly limited and are preferably alkaline conditions. The lower limit of the alkaline conditions is, for example, preferably about pH 9, more preferably about pH 11. The upper limit of the alkaline conditions is not particularly limited and is, for example, preferably about pH 12. The pH conditions for solubilization can be set as appropriate according to the kind of the chelating agent to be used, for example.

In the case where both of the pH conditions for insolubilization in the step of forming a complex and the pH conditions for solubilization in the step of recovering the metal are alkaline conditions, the latter alkaline conditions are preferably at a pH higher than the former pH conditions. In this case, the difference between the pH conditions for insolubilization in the step of forming a complex and the pH conditions for solubilization in the step of recovering the metal are, for example, about 1 or more, such as about 3 or more, such as about 5 or more, or for example, about 8 or less.

A method for dissolving the complex is not particularly limited. For example, the complex may be dissolved by adding the aqueous medium where the pH conditions have been previously adjusted to the pH conditions for solubilization to the complex or by adding the complex to the aqueous medium and thereafter adjusting the pH conditions of the mixture thus obtained to the pH conditions for solubilization.

A method for adjusting the pH conditions to the pH conditions for solubilization is not particularly limited. For the adjustment, an alkaline reagent can be used, for example. Examples of the alkaline reagent include an alkali, an alkali aqueous solution, and a buffer solution under alkaline conditions. The alkali is not particularly limited, and examples thereof include sodium hydroxide and potassium hydroxide. The alkali aqueous solution can be, for example, one obtained by diluting an alkali with water or a buffer solution. The buffer solution for use in the dilution of the alkali is not particularly limited, and any of the above-mentioned general buffer solutions can be used. The concentration of the alkali in the alkali aqueous solution is not particularly limited and is, for example, from about 0.1N to about 1N. The buffer solution under alkaline conditions is not particularly limited, and examples thereof include Tris-NaOH, Tris-HCl, a carbonate buffer solution, and Good buffer solutions. The concentration of the buffer solution under alkaline conditions is not particularly limited and is, for example, from about 10 to about 100 mmol/L.

A method for mixing the complex and the aqueous medium is not particularly limited, and examples thereof include conventional methods such as mixing by repeatedly turning upside down, mixing by vibrating, and mixing by ultrasound.

The amount of the aqueous medium to be added to the complex is not particularly limited and is, for example, preferably the amount in which the recovered complex can be dissolved. The amount of the aqueous medium to be added is, for example, preferably less than the fluid amount of the sample. With this amount, a metal-containing liquid with the metal concentration higher than the sample can be obtained, for example. That is, a metal-containing liquid in which the metal is concentrated as compared with in the sample can be obtained. The amount of the aqueous medium to be added with respect to the fluid amount of the sample is, for example, in the range from 1/2 to 1/100, preferably from 1/10 to 1/100, more preferably from 1/50 to 1/100.

In the metal recovering method of the present invention, the step of recovering the metal may further include the step of decomposing the chelating agent being in the complex after dissolving the complex in an aqueous medium. By decomposing the chelating agent, a single metal can be recovered from the complex. A method for decomposing the chelating agent is not particularly limited and can be, for example, a conventionally known method such as ashing. Examples of the ashing include wet ashing and dry ashing. The wet ashing can be performed according to the Mercury Analysis Manual (Ministry of the Environment, March 2004), for example.

The metal recovering method of the present invention is described below with reference to, as an example, a method for recovering mercury as a metal, using the acidic conditions as the pH conditions for insolubilization, the alkaline conditions as the pH conditions for solubilization, and an urine sample as the sample. This, however, is a mere example, and the present invention is by no means limited thereto.

First, the pH of an urine sample is adjusted to acidic conditions by adding an acidic reagent thereto.

The amount of the urine sample is not particularly limited and is, for example, in the range from 1 to 100 mL, preferably from 1 to 20 mL, more preferably from 5 to 10 mL. The pH of the urine sample is adjusted to, for example, preferably from about 1 to about 4, more preferably from about 1 to about 2. The amount of the acidic reagent to be added is not particularly limited and is, for example, in the range from 1 to 10 µL per 1 mL of the urine sample. The acidic reagent is, for example, preferably a hydrochloric acid aqueous solution, and the normality thereof is, for example, in the range from about 1N to about 8N.

A dried chelating agent obtained by freeze-drying is placed in a tube, and further, an urine sample whose pH has been adjusted is added thereto. Thus, a mixture is prepared. The amount of the chelating agent is, for example, from 0.1 to 2 mg per 1 mL of the urine sample. At that time, the pH of the mixture is, for example, from about 1 to about 4, preferably from about 1 to about 2. In the case where the chelating agent is represented by the structural formula (1), preferably dithizone, the amount of the chelating agent is, for example, from 0.1 to 1.5 mg, preferably from 0.1 to 0.3 mg, more preferably 0.3 mg, per 1 mL of the urine sample. At that time, the pH of the mixture is, for example, from about 1 to about 4, preferably from about 1 to about 2. In the case where the chelating agent is represented by the structural formula (2), preferably glyoxaldithiosemicarbazone, the amount of the chelating agent is, for example, in the range from 0.3 to 2 mg, preferably from 1 to 2 mg per 1 mL of the urine sample. At that time, the pH of the mixture is, for example, from about 1 to about 4, preferably from about 1 to about 2.

The prepared mixture is stood for the predetermined time, so that a complex between the chelating agent and mercury being in the urine sample is formed. The treatment temperature is, for example, room temperature, and the treatment time is, for example, from 10 seconds to 120 minutes. Specifically, the treatment time is, for example, preferably in the range from 10 seconds to 10 minutes, particularly preferably from 10 seconds to 5 minutes.

Then, the mixture is subjected to centrifugation, so that a precipitate containing the complex is separated from a supernatant. Thereafter, the supernatant is removed, and an alkaline reagent is added in the tube containing the complex, so that the complex is dissolved in the alkaline reagent.

The amount of the alkaline reagent to be added is not particularly limited and is, for example, in the range from 10 to 200 µL, preferably from 20 to 100 µL, more preferably 20 µL, per 1 mL of the urine sample. The pH of the alkaline reagent is, for example, from about 9 to about 12, preferably from about 11 to about 12. The alkaline reagent is, for example, preferably a sodium hydroxide aqueous solution, and the normality thereof is, for example, in the range from about 0.1N to about 1N, preferably about 0.4N.

As described above, mercury in the state of being a complex, being dissolved in the aqueous solution, can be recovered. Only mercury can be recovered by decomposing the chelating agent in the complex by wet ashing, for example. An example of recovering mercury is explained above, and the present invention, however, is by no means limited thereto. In the metal recovering method of the present invention, two or more kinds of metals can be recovered at the same time by a single recovering treatment, for example. According to the metal recovering method of the present invention, for example, mercury and one or more kinds of the other metals can be recovered at the same time, or two or more kinds of metals other than mercury can be recovered at the same time.

<Method for Analyzing Metal>

The method for analyzing a metal (hereinafter merely referred to as the "metal analyzing method") of the present invention is a method for analyzing a metal, the method including the steps of recovering a metal from a sample by the metal recovering method of the present invention; and analyzing the metal. The step of recovering a metal can be explained with reference to the explanation of the metal recovering method of the present invention.

The step of analyzing the metal is not particularly limited and can be selected as appropriate according to the kind of the metal to be analyzed, for example. The analysis of the metal can be performed by, for example, an optical measurement, GC-ECD (gas chromatography-electron capture detector), an electrochemical measurement (e.g., stripping voltammetry), a mass spectrometer, or the like. The analysis by the optical measurement can be performed by measuring an absorbance, a transmittance, a reflectance, or the like using an optical analyzer, for example. Examples of the optical analyzer include an atomic absorption spectrometer, a visible spectrometer, and ICP-AES (Inductively Coupled Plasma Atomic Emission Spectrometer). The analysis of the metal may be qualitative analysis or quantitative analysis, for example.

The metal analyzing method of the present invention may further include the step of correcting a measurement value, for example. In the step of correcting a measurement value, a measurement value as a measurement result can be corrected according to the correlation between the measurement value and the metal concentration in a sample, for example. The correlation can be obtained as follows, for example. A metal in the standard samples with the known metal concentrations is recovered by the metal recovering method of the present invention, and measurement values of the metal and the corresponding metal concentrations are plotted. It is preferred that the standard samples are in a dilution series. By correcting measurement values as described above, it becomes possible to perform the quantitative determination with higher reliability.

The metal as the above-mentioned complex may be analyzed, or the metal as a single metal obtained by isolating the metal from the complex may be analyzed, for example. In the latter case, it is preferred that the step of recovering the metal includes the step of decomposing the chelating agent being in the complex, i.e., the step of isolating the metal from the complex.

<Reagent for Recovery of Metal>

The reagent for recovery of a metal of the present invention is a reagent for recovery of a metal, for use in the metal recovering method of the present invention, the reagent containing: a chelating agent. The chelating agent can be explained with reference to the explanation of the metal recovering method of the present invention, for example.

<Kit for Recovery of Metal>

The kit for recovery of a metal of the present invention is a kit for recovery of a metal, for use in the metal recovering method of the present invention, the kit including: a chelating agent; and a pH adjusting reagent. The pH adjusting reagent is not particularly limited and is, for example, an acidic reagent, a neutral reagent, and/or an alkaline reagent. The chelating agent, the acidic reagent, the neutral reagent, and the alkaline reagent can be explained with reference to the explanation of the metal recovering method of the present invention, for example. It is preferred that the chelating agent and the pH adjusting reagent are stored in different containers.

The kit may further include other reagent besides the chelating agent and the pH adjusting reagent, for example. The other reagent is not particularly limited, and examples thereof include the oxidizing agent and the reducing agent such as mentioned above.

<Analysis Apparatus>

The analysis apparatus of the present invention is, as mentioned above, an analysis apparatus including: a pH adjusting unit for adjusting a pH; a mixing unit for mixing a chelating agent and a sample; a complex recovering unit for recovering a complex between the chelating agent and a metal present in the sample from a mixture containing the chelating agent and the sample; an adding unit for adding an aqueous medium to the recovered complex; a metal recovering unit for recovering the metal present in the complex; and an analyzing unit for analyzing the recovered metal, wherein the analysis apparatus is for use in a method for analyzing a metal. Specifically, it is preferred that the analysis apparatus of the present invention is for use in the method for analyzing a metal of the present invention. The pH adjusting unit includes an acid adding unit and an alkali adding unit, for example. The chelating agent can be explained with reference to the explanation of the metal recovering method of the present invention, for example.

The acid adding unit includes: a suction-and-discharge unit for sucking and discharging an acidic reagent arranged inside or outside the analysis apparatus; and a controlling unit for controlling the amount of the acidic reagent to be sucked and/or discharged, for example. The suction-and-discharge unit can be, for example, a pump. The controlling unit can be, for example, a valve.

The alkali adding unit includes: a suction-and-discharge unit for sucking and discharging an alkaline reagent arranged inside or outside the analysis apparatus; and a controlling unit for controlling the amount the alkaline reagent to be sucked and/or discharged, for example. The suction-and-discharge unit and the controlling unit can be, for example, the same as mentioned above. The alkali adding unit may also serve as the acid adding unit.

Examples of the mixing unit include a stirrer, a suction-and-discharge unit, a shaker, and an ultrasound generator.

Examples of the complex recovering unit include a centrifuge, a filtration unit, and a freeze-dryer.

The adding unit includes: a suction-and-discharge unit for sucking and discharging the aqueous medium arranged inside or outside the analysis apparatus; and a controlling unit for controlling the amount of the aqueous medium to be sucked and/or discharged, for example. The suction-and-discharge unit and the controlling unit can be, for example, the same as mentioned above. The adding unit may also serve as an alkali adding unit.

The metal recovering unit is, for example, a unit for decomposing the chelating agent in the complex. Examples of the unit include ashers such as a wet asher and a dry asher.

The analyzing unit can be, for example, an optical analyzer, and specific examples thereof include an atomic absorption spectrometer and a visible spectrometer.

The analysis apparatus of the present invention preferably further include a pH measuring unit. The pH measuring unit can be, for example, a pH meter. The analysis apparatus of the present invention preferably includes an introducing unit for introducing a sample, for example. The introducing unit is, for example, preferably a suction-and-discharge unit for sucking and discharging a sample.

According to the analysis apparatus of the present invention, the above-mentioned metal analyzing method of the present invention can be performed. The usage of the analysis apparatus of the present invention is illustrated below. The present invention, however, is by no means limited thereto.

A sample, a chelating agent, an aqueous medium, and an acidic reagent and alkali reagent as a pH adjusting reagent are arranged inside or outside the analysis apparatus.

First, the pH of the sample is adjusted to acidic conditions by adding the acidic reagent to the sample using the acid adding unit. Then, the sample is introduced into the chelating agent using the introducing unit, and the sample and the chelating agent are mixed using the mixing unit. Thus, a mixture is prepared. Thereafter, a complex in the mixture is recovered using the complex recovering unit. The aqueous medium is added to the recovered complex using the adding unit, and further, in the alkali adding unit, the pH of the aqueous medium is adjusted so that the aqueous medium is under alkaline conditions. Thus, the complex is dissolved in the aqueous medium. Subsequently, the chelating agent in the complex aqueous solution in which this complex is dissolved is decomposed using the metal recovering unit. Thus, a metal is recovered. Then, the recovered metal is analyzed using the analyzing unit. As described above, according to the analysis apparatus of the present invention, the metal analyzing method of the present invention can be performed automatically.

The analysis apparatus of the present invention may further include an output unit for outputting an analysis result with respect to the metal, for example. As the output unit, a monitor or a printer can be used, for example.

EXAMPLES

Next, the examples of the present invention are described. The present invention, however, is by no means limited thereto.

Example A1

(1) Preparation of Urine Sample

Mercury chloride (produced by Wako Pure Chemical Industries, Ltd.) was mixed with pooled urine (pH 6 to 7) collected from a healthy male so as to have predetermined mercury concentrations. Thus, urine samples were obtained. The respective predetermined mercury concentrations were 1, 10, 100 μg/L. The pH's of the urine samples each containing the mercury chloride added thereto were 5 to 7. Then, 60 μL of 5N hydrochloric acid (produced by NACALAI TESQUE, INC.) was mixed with 5 mL each of the urine samples, so that the pH's of the urine samples were adjusted to 1 to 2.

(2) Preparation of Chelating Agent

Dithizone (produced by Fluka) was dissolved in t-butyl alcohol (produced by NACALAI TESQUE, INC.). This solution thus obtained was dispensed in 15 mL-capacity conical tubes made of PP (produced by Nunc) so that the amount of the dithizone in each of the tubes became 1.5 mg. The tubes each containing the solution was then subjected to freeze-drying.

(3) Recovery of Mercury from Urine Sample 5 mL each of the urine samples was added to each of the tubes, which was then shaken for 5 minutes at room temperature so as to mix the urine sample and the dithizone. Thus, a complex between the dithizone and mercury was formed. The tubes were then subjected to centrifugation (19,600 m/s$^2$ (2000×g), 20° C., 10 minutes) so as to separate each mixture into a precipitate containing the complex and a supernatant. The supernatant was removed, and thereafter 0.1 mL of a 0.4N NaOH aqueous solution (pH 12) was added to each of the tubes, which was then repeatedly turning upside down so as to mix the precipitate and the NaOH aqueous solution. Thus, the complex in the precipitate was dissolved. Aqueous solutions (pH 12) each containing the complex dissolved therein were used as mercury-concentrated samples.

The mercury-concentrated samples were subjected to wet ashing. Thus, the dithizone in the complex was decomposed. The wet ashing was performed according to the Mercury Analysis Manual (Ministry of the Environment, March 2004) (the same applies hereinafter.). Then, the mercury concentration of each of the mercury-concentrated samples thus obtained was determined using an atomic absorption spectrometer (trade name: MERCURY ANALYZER, produced by Nippon Instruments, Co., Ltd.). Furthermore, the mercury concentration of each of the urine samples was determined in the same manner as described above using the atomic absorption spectrometer.

Then, the mercury concentration ($X_C$) and volume ($X_V$) of each of the mercury-concentrated samples and the mercury concentration ($Y_C$) and volume ($Y_V$) of each of the urine samples were substituted into the following formula (1). Thus, the recovery rate (%) of mercury was determined. Furthermore, the mercury concentration ($X_C$) of each of the mercury-concentrated samples and the mercury concentration ($Y_C$) of each of the urine samples were substituted into the following formula (2). Thus, the concentration rate (–fold) of mercury was determined.

Recovery rate (%)=100×($X_C$×$X_V$)/($Y_C$×$Y_V$)  (1)

Concentration rate (–fold)=$X_C$/$Y_C$  (2)

The recovery rate and concentration rate of mercury with respect to each of the urine samples is shown in Table 1 below. As shown in Table 1, mercury was recovered from all of the urine samples. From these results, it was found that according to the present invention, mercury could be recovered from the urine samples without requiring the use of an organic medium. The recovery rates and concentration rates of mercury were determined with respect to a total of three urine samples each with the mercury concentration of 100 µg/L in the same manner as described above. The C.V. of the recovery rate and the C.V. of the concentration rate were 3.7%. Thus, it was confirmed that the recovery rates and concentration rates of mercury with respect to the urine samples each with the mercury concentration of 100 µg/L showed sufficient repeatability.

TABLE 1

|  | Mercury concentration in urine sample (µg/L) | | |
| --- | --- | --- | --- |
|  | 1 | 10 | 100 |
| Recovery rate (%) | 48.8 | 59.4 | 63.7 |
| Concentration rate (–fold) | 24.4 | 29.7 | 31.9 |

Example A2

Urine samples (n=2) each with the mercury concentration of 10 µg/L were prepared in the same manner as in Example A1. Then, mercury-concentrated samples were prepared in the same manner as in Example A1 except that 0.5 mL of a 0.08N NaOH aqueous solution (pH 12) was used as a NaOH aqueous solution as substitute for 0.1 mL of the 0.4N NaOH aqueous solution. Thereafter, the mercury concentration of each of the mercury concentrated samples and urine samples and the recovery rate (%) and concentration rate (–fold) of mercury were determined in the same manner as in Example A1.

The recovery rate and concentration rate of mercury with respect to each of the urine samples is shown in Table 2 below. As shown in Table 2, according to the present example, mercury could be concentrated and recovered with high recovery rate and high repeatability without requiring the use of an organic medium.

TABLE 2

|  | Concentrated sample | |
| --- | --- | --- |
|  | No. 1 | No. 2 |
| Recovery rate (%) | 85.4 | 88.7 |
| Concentration rate (–fold) | 8.5 | 8.9 |

Example A3

(1) Preparation of Urine Sample

The urine samples with the respective mercury concentrations of 1 and 10 µg/L were prepared in the same manner as in Example 1. 5N hydrochloric acid (produced by NACALAI TESQUE, INC.) was added to 5 mL each of the urine samples, so that the pH's of the urine samples were adjusted to 2 or 4.

(2) Preparation of Chelating Agent

Dithizone (produced by Fluka) was dissolved in 2-propanol (produced by NACALAI TESQUE, INC.). This solution thus obtained was dispensed in 15 mL-capacity conical tubes made of PP (produced by Nunc) so that the amount of the dithizone in each of the tubes became 1.5 mg. The tubes each containing the solution were then subjected to freeze-drying.

(3) Recovery of Mercury from Urine Sample

Mercury-concentrated samples were prepared, and the mercury concentration of each of the mercury-concentrated samples and urine samples was determined, in the same manner as in Example A1. Then, the recovery rate (%) and concentration rate (–fold) of mercury were determined in the same manner as in Example A1. In order to dissolve the formed complex, 0.5 mL of a 0.08N NaOH aqueous solution (pH 12) was used as substitute for the 0.4N NaOH aqueous solution. Aqueous solutions (pH 12) each containing the complex dissolved therein were used as the mercury-concentrated samples.

The recovery rate and concentration rate of mercury with respect to each of the urine samples is shown in Table 3 below. As shown in Table 3, according to the present example, mercury was concentrated and recovered with the high recovery rates without requiring the use of an organic medium in the case where the complex between the dithizone and mercury was formed under the pH conditions of 2 and 4.

TABLE 3

|  | pH at the time of forming complex | | | |
| --- | --- | --- | --- | --- |
|  | 2 | | 4 | |
|  | Mercury concentration in urine sample (μg/L) | | | |
|  | 1 | 10 | 1 | 10 |
| Recovery rate (%) | 87.3 | 86.3 | 69.1 | 78.8 |
| Concentration rate (-fold) | 43.6 | 43.1 | 34.6 | 39.4 |

Example A4

(1) Preparation of Urine Sample

Urine samples each with the mercury concentration of 10 μg/L were prepared in the same manner as in Example A1. 5N hydrochloric acid (produced by NACALAI TESQUE, INC.) or 5N sodium hydroxide (produced by NACALAI TESQUE, INC.) was added to 5 mL each of the urine samples so that the pH's of the respective urine samples were adjusted to 2, 3, 4, 6.8, and 8. Furthermore, as negative controls, five types of distilled waters with the respective pH's of 2, 3, 4, 6.8, and 8 were used. For the adjustment of the pH's of the distilled waters, 5N hydrochloric acid (produced by NACALAI TESQUE, INC.) or 5N sodium hydroxide (produced by NACALAI TESQUE, INC.) was used as in the adjustment of the pH's of the urine samples.

(2) Preparation of Chelating Agent

Dithizone was freeze-dried in the same manner as in Example A1.

(3) Recovery of Mercury from Urine Sample

Mercury-concentrated samples were prepared in the same manner as in Example A1. Then, the mercury-concentrated samples were subjected to ashing, and thereafter mercury in each of the mercury-concentrated samples thus obtained was qualitatively determined using an atomic absorption spectrometer.

The results of these are shown in Table 4 below. Mercury was not detected in any of the negative controls (−). In contrast, mercury was detected in all of the mercury-concentrated samples obtained through the formation of complexes under the respective pH conditions (+). From these results, it was found that mercury was recovered from the urine samples without requiring the use of an organic medium in the case where the complex was formed in the wide pH range from 2 to 8.

TABLE 4

| pH at the time of forming complex | Determination |
| --- | --- |
| 2 | + |
| 3 | + |
| 4 | + |
| 6.8 | + |
| 8 | + |
| Control | − |

+: Mercury could be detected.
−: Mercury could not be detected.

Example B1

(1) Preparation of Urine Sample

Mercury chloride (produced by Wako Pure Chemical Industries, Ltd.) was mixed with pooled urine (pH 6 to 7) collected from a healthy male so as to have a predetermined mercury concentration. Thus, an urine sample was obtained. The predetermined mercury concentration was 10 μg/L. The pH of the urine sample containing the mercury chloride added thereto was 5 to 7. Then, 60 μL of 5N hydrochloric acid (produced by NACALAI TESQUE, INC.) was mixed with 5 mL of the urine sample, so that the pH of the urine sample was adjusted to 1 to 2.

(2) Preparation of Chelating Agent

Glyoxaldithiosemicarbazone (chelating agent a) (produced by Wako Pure Chemical Industries, Ltd.) was dissolved in t-butyl alcohol (produced by NACALAI TESQUE, INC.), and (1E,2E)-aminocarbothioyl hydrazono phenylethanal thiosemicarbazone (chelating agent b) (produced by SIGMA-ALDRICH) was dissolved in t-butyl alcohol. Each of these solutions thus obtained was dispensed in 15 mL-capacity conical tubes made of PP (produced by Nunc) so that the amount of the chelating agent a or the chelating agent b in each of the tubes became 1.5 mg. The tubes containing each of the solutions were then subjected to freeze-drying.

(3) Recovery of Mercury from Urine Sample 5 mL of the urine sample was added to each of the tubes, which was then shaken for 5 minutes at room temperature so as to mix the urine sample and the chelating agent a and mix the urine sample and the chelating agent b. Thus, a complex between the chelating agent a and mercury and a complex between the chelating agent b and mercury were formed. The tubes were then subjected to centrifugation (19,600 m/s$^2$ (2000×g), 20° C., 10 minutes) so as to separate each mixture into a precipitate containing the complex and a supernatant. The supernatant was removed, and thereafter 0.1 mL of a 0.4N NaOH aqueous solution (pH 12) was added to each of the tubes, which was then repeatedly turning upside down so as to mix the precipitate and the NaOH aqueous solution. Thus, the complex in the precipitate was dissolved. Aqueous solutions (pH 12) each containing each of the complexes dissolved therein were used as mercury-concentrated samples.

The mercury-concentrated samples were subjected to wet ashing. Thus, the chelating agent a and the chelating agent b in the respective complexes were decomposed. Then, the mercury concentration of each of the mercury-concentrated samples thus obtained was determined using an atomic absorption spectrometer (trade name: MERCURY ANALYZER, produced by Nippon Instruments, Co., Ltd.). Furthermore, the mercury concentration of the urine sample was determined in the same manner as described above using the atomic absorption spectrometer.

Then, the mercury concentration ($X_C$) and volume ($X_V$) of each of the mercury-concentrated samples and the mercury concentration ($Y_C$) and volume ($Y_V$) of the urine sample were substituted into the following formula (1). Thus, the recovery rate (%) of mercury was determined. Furthermore, the mercury concentration ($X_C$) of each of the mercury-concentrated samples and the mercury concentration ($Y_C$) of the urine sample were substituted into the following formula (2). Thus, the concentration rate (-fold) of mercury was determined.

$$\text{Recovery rate (\%)} = 100 \times (X_C \times X_V)/(Y_C \times Y_V) \qquad (1)$$

$$\text{Concentration rate (-fold)} = X_C/Y_C \qquad (2)$$

The recovery rate and concentration rate of mercury with respect to the urine sample is shown in Table 5 below. As shown in Table 5, mercury was recovered from the urine sample. From these results, it was found that according to the present invention, mercury could be recovered from the urine samples without requiring the use of an organic medium.

TABLE 5

| | | Chelating agent a | Chelating agent b |
|---|---|---|---|
| Mercury concentration (μg/L) | before concentration | 9.37 | 9.37 |
| | after concentration | 186.31 | 115.09 |
| Recovery rate (%) | | 39.77 | 24.57 |
| Concentration rate (-fold) | | 19.88 | 12.28 |

Example C1

(1) Preparation of Liquid Sample

A 0.34 mol/L sodium chloride aqueous solution containing 0.01% poly(oxyethylene)sorbitan monolaurate (Tween-20) was prepared. A lead standard solution (produced by Wako Pure Chemical Industries, Ltd.) was added to the aqueous solution thus obtained so as to have the lead concentration of 0.5 mg/L. Thus, a liquid sample was prepared. On the other hand, a control sample (with the leas concentration of 0 mg/L) was prepared by adding a 0.1 mol/L nitric acid aqueous solution as substitute for the lead standard solution. The pH's of the liquid sample and the control sample were 6.

(2) Preparation of Chelating Agent

Dithizone (produced by Fluka) was dissolved in t-butyl alcohol (produced by NACALAI TESQUE, INC.). This solution thus obtained was dispensed in 1 mL-capacity tubes made of PP (produced by produced by Nichiryo Co., Ltd.) so that the amount of the dithizone in each of the tubes became 1.5 mg. The tubes each containing the solution were then subjected to freeze-drying.

(3) Recover of Lead from Liquid Sample 1 mL of the liquid sample was added to one of the tubes, which was then shaken for 5 minutes at room temperature so as to mix the liquid sample and the dithizone. Thereafter, the tube was stood still for 2 hours, so that a complex between the dithizone and lead was formed. The tube was then subjected to centrifugation (19,600 m/s² (2000×g), 20° C., 10 minutes) so as to separate the mixture into a precipitate containing the complex and a supernatant. The supernatant was removed, and thereafter 0.1 mL of a 0.1 mol/L nitric acid aqueous solution was added to the tube. Under the same conditions as mentioned above, the precipitate and the nitric acid aqueous solution were mixed in the tube, and then the tube was subjected to centrifugation so as to separate the mixture into a precipitate containing the complex and a supernatant. Then, the supernatant was removed, and thereafter 0.1 mL of a 0.4N NaOH aqueous solution (pH 12) was added to the tube, which was then repeatedly turning upside down so as to mix the precipitate and the NaOH aqueous solution. Thus, the complex in the precipitate was dissolved. An aqueous solution (pH 12) containing the complex dissolved therein was used as a lead-concentrated sample.

The lead-concentrated sample was subjected to wet ashing. Thus, the dithizone in the complex was decomposed. Then, the lead concentration of the lead-concentrated sample thus obtained was determined by mass spectrometry using an ICP mass spectrometer (ICP-MS, trade name: ICPM-8500, produced by Shimadzu Corporation). Furthermore, the lead concentration of the control sample was determined in the same manner as described above.

Then, the lead concentration ($X_C$) and volume ($X_V$) of the lead-concentrated sample and the lead concentration ($Y_C$) and volume ($Y_V$) of the liquid sample were substituted into the following formula (3). Thus, the recovery rate (%) of lead was determined. Furthermore, the lead concentration ($X_C$) of the lead-concentrated sample and the lead concentration ($Y_C$) of the liquid sample were substituted into the following formula (4). Thus, the concentration rate (-fold) of lead was determined.

$$\text{Recovery rate (\%)} = 100 \times (X_C \times X_V)/(Y_C \times Y_V) \qquad (1)$$

$$\text{Concentration rate (-fold)} = X_C/Y_C \qquad (2)$$

The recovery rate and concentration rate of lead with respect to each of the liquid sample (with the lead concentration of 0.5 mg/L) and control sample (with the lead concentration of 0 mg/L) is shown in Table 6 below. As shown in Table 6, lead was recovered from the liquid sample. From this result, it was found that according to the present invention, lead could be recovered from the liquid sample without requiring the use of an organic medium.

TABLE 6

| | | Lead concentration in liquid sample (mg/L) | |
|---|---|---|---|
| | | 0 | 0.5 |
| Lead concentration (mg/L) | before concentration | −0.02 | 0.49 |
| | after concentration | 0.01 | 1.04 |
| Recovery rate (%) | | — | 21.03 |
| Concentration rate (-fold) | | — | 2.10 |

As described above, according to the present invention, a metal can be recovered easily by utilizing the difference in solubility of the chelating agent in an aqueous medium according to the difference in pH conditions without substantially using an organic medium. Therefore, the present invention is really useful in critical examinations of samples derived from biological bodies and environmental testing, for example.

The invention may be embodied in other forms without departing from the spirit or essential characteristics thereof.

The embodiments disclosed in this application are to be considered in all respects as illustrative and not limiting. The scope of the invention is indicated by the appended claims rather than by the foregoing description, and all changes which come within the meaning and range of equivalency of the claims are intended to be embraced therein.

What is claimed is:

1. A method for recovering a metal, the method comprising the steps of:
    forming a complex in an aqueous medium between a chelating agent and a metal present in a sample in a mixture prepared by mixing the chelating agent and the sample under pH conditions where the chelating agent is substantially insoluble in the aqueous medium;
    recovering the complex from the mixture; and
    recovering the metal by dissolving the recovered complex in an aqueous medium under pH conditions that are different from the pH conditions where the chelating agent is substantially insoluble in an aqueous medium.

2. The method according to claim 1, wherein the chelating agent is a chelating agent comprising a sulfur-containing group.

3. The method according to claim 2, wherein the sulfur-containing group comprises a thioketone group.

4. The method according to claim 1, wherein the chelating agent is at least one selected from the group consisting of a thiocarbazone group, a thiosemicarbazone group, a thiocarbadiazone group, a thiourea group, a thiosemicarbazide group, and a rubeamate group.

5. The method according to claim 1, wherein the chelating agent is selected from the group consisting of at least one of 1,5-diphenyl-3-thiocarbazone, glyoxaldithiosemicarbazone, and (1E,2E)-aminocarbothioyl hydrazono phenylethanal thiosemicarbazone.

6. The method according to claim 1, wherein in the step of forming a complex, the complex is formed by adjusting the pH conditions of the sample to the pH conditions where the chelating agent is substantially insoluble in the aqueous medium and thereafter preparing the mixture by mixing the sample and the chelating agent.

7. The method according to claim 1, wherein the pH conditions where the chelating agent is substantially insoluble in the aqueous medium are about pH 8 or less.

8. The method according to claim 7, wherein the pH conditions where the chelating agent is substantially insoluble in the aqueous medium are about pH 4 or less.

9. The method according to claim 1, wherein the pH conditions that are different from the pH conditions where the chelating agent is substantially insoluble in an aqueous medium are about pH 9 or more.

10. The method according to claim 1, wherein the metal is at least one selected from the group consisting of Bi, Hg, Cd, Pd, Zn, Tl, Ag, Pb, and As.

11. The method according to claim 1, wherein the amount of the aqueous medium used in the step of recovering the metal is less than a fluid amount of the sample.

12. The method according to claim 1, wherein the step of recovering the metal further includes the step of decomposing the chelating agent in the complex after dissolving the complex in an aqueous medium.

* * * * *